US011440977B2

(12) United States Patent
Sauty et al.

(10) Patent No.: US 11,440,977 B2
(45) Date of Patent: Sep. 13, 2022

(54) GUAYULE LATEX EXTRUSION

(71) Applicant: Cooper Tire & Rubber Company, Findlay, OH (US)

(72) Inventors: Nicolas Sauty, Perrysburg, OH (US); Brittney Sunday, Libertyville, IL (US); Howard Colvin, Wayne, OH (US)

(73) Assignee: Cooper Tire & Rubber Company, Findlay, OH (US)

( * ) Notice: Subject to any disclaimer, the term of this patent is extended or adjusted under 35 U.S.C. 154(b) by 561 days.

(21) Appl. No.: 15/895,601

(22) Filed: Feb. 13, 2018

(65) Prior Publication Data

US 2018/0230243 A1    Aug. 16, 2018

Related U.S. Application Data

(60) Provisional application No. 62/458,300, filed on Feb. 13, 2017.

(51) Int. Cl.

| | |
|---|---|
| *C07C 49/08* | (2006.01) |
| *C07C 9/14* | (2006.01) |
| *C08C 1/15* | (2006.01) |
| *C08C 3/02* | (2006.01) |
| *B29B 7/80* | (2006.01) |
| *B29C 48/00* | (2019.01) |
| *B29B 7/86* | (2006.01) |
| *B29B 7/74* | (2006.01) |
| *B29C 48/03* | (2019.01) |
| *B29B 7/84* | (2006.01) |
| *B29B 7/00* | (2006.01) |
| *B29C 48/76* | (2019.01) |
| *B29B 7/40* | (2006.01) |
| *B29B 9/06* | (2006.01) |
| *B29B 7/46* | (2006.01) |
| *B29K 105/00* | (2006.01) |

(52) U.S. Cl.
CPC ............... *C08C 1/15* (2013.01); *B29B 7/007* (2013.01); *B29B 7/7495* (2013.01); *B29B 7/80* (2013.01); *B29B 7/842* (2013.01); *B29B 7/86* (2013.01); *B29C 48/0022* (2019.02); *B29C 48/022* (2019.02); *B29C 48/03* (2019.02); *B29C 48/767* (2019.02); *C07C 9/14* (2013.01); *C07C 49/08* (2013.01); *C08C 3/02* (2013.01); *B29B 7/40* (2013.01); *B29B 7/46* (2013.01); *B29B 7/805* (2013.01); *B29B 9/06* (2013.01); *B29C 48/762* (2019.02); *B29K 2105/0064* (2013.01)

(58) Field of Classification Search
CPC .... C08C 1/15; C08C 3/02; C07C 9/14; C07C 49/08
See application file for complete search history.

(56) References Cited

U.S. PATENT DOCUMENTS

| | | | |
|---|---|---|---|
| 2,408,853 | A | 10/1946 | Hoover et al. |
| 2,618,670 | A | 11/1952 | Clark |
| 3,742,093 | A | 6/1973 | Skidmore |
| 4,103,074 | A | 7/1978 | Hertel et al. |
| 4,110,843 | A | 8/1978 | Skidmore |
| 4,136,131 | A | 1/1979 | Buchanan |
| 4,148,991 | A | 4/1979 | Skidmore |
| 4,435,337 | A | 3/1984 | Kay et al. |
| 4,446,094 | A | 5/1984 | Rossiter |
| 4,623,713 | A | 11/1986 | Beinor et al. |
| 4,684,715 | A | 8/1987 | Kay et al. |
| 5,580,942 | A | 12/1996 | Cornish |
| 8,815,965 | B2 | 8/2014 | Cole et al. |
| 9,273,153 | B2 | 3/2016 | Martin et al. |
| 9,315,589 | B2 | 4/2016 | Huang et al. |
| 2006/0073319 | A1 | 4/2006 | Roberson et al. |
| 2012/0329923 | A1 | 12/2012 | Fen et al. |
| 2014/0213696 | A1 | 7/2014 | Martin et al. |
| 2014/0288255 | A1 | 9/2014 | Martin et al. |
| 2015/0141576 | A1 | 5/2015 | Choi et al. |
| 2015/0232583 | A1 | 8/2015 | Fraley et al. |

FOREIGN PATENT DOCUMENTS

| | | |
|---|---|---|
| CN | 102066424 B | 1/2014 |
| EP | 0892705 A2 | 1/1999 |
| JP | 62502 A | 1/1987 |
| JP | 2011516716 A | 5/2011 |
| WO | 2016040665 A1 | 3/2016 |

(Continued)

OTHER PUBLICATIONS

Nichols, R.J. et al Advances in Polymer Technology vol. 3(1) pp. 41-49 (Year: 1983).*
W.W. Schloman Jr., Processing Guayule for Latex and Bulk Rubber, Science Direct; Industrial Crops and Products 22 (2005) 41-47, www.elsevier.com/locate/indcrop; Department of Chemistry, The University of Akron, Akron, Ohio—Elsevier B.V. 2004.
C.H. Pearson et al., Extraction of Natural Rubber and Resin from Guayule Using an Accelerated Solvent Extractor, SciVerse ScienceDirect; Industrial Crops and Products 43 (2013) 506-510, www.elsevier.com/locate/indcrop; Colorado State University, Agricultural Experiment Station, Fruita, CO—Elsevier B.V. 2012.

(Continued)

*Primary Examiner* — Irina S Zemel
*Assistant Examiner* — Jeffrey S Lenihan
(74) *Attorney, Agent, or Firm* — Mandy B. Willis

(57) ABSTRACT

A latex processing system and method involves mixing a latex and at least one solvent blend in an extruder, in order to remove resin found in the latex and to coagulate the latex to form a coagulum. The at least one solvent blend has a first solvent configured to coagulate the latex, and a second solvent configured to swell the resulting coagulum. In particular, a series of the solvent blends may be used at different locations along a length of the extruder, and may further include distinct blends of the first solvent and the second solvent, introduced at the different locations, and having different ratios of the first solvent and the second solvent.

14 Claims, 2 Drawing Sheets

(56) References Cited

FOREIGN PATENT DOCUMENTS

WO      2016062753 A1    4/2016
WO      2016162645 A2    10/2016

OTHER PUBLICATIONS

A.K. Ghosh and J.T. Lindt, Processing of ABS Latex in a Single Screw Extruder, Hanser eLibrary.com http://www.hanser-elibrary.com/doi/abs/10.3139/217.900195. International Polymer Processing: vol. 5, No. 3, pp. 195-200, Department of Material Science & Engineering Dept., Pittsburgh, PA.

* cited by examiner

GUAYULE LATEX EXTRUSION

CROSS-REFERENCE TO RELATED APPLICATIONS

This application claims the benefit of U.S. Provisional Application No. 62/458,300, filed on Feb. 13, 2017. The entire disclosure of the above application is hereby incorporated herein by reference.

FIELD

The present disclosure relates to systems and methods for extracting natural rubber latex from non-Hevea plants and, more particularly, an extrusion-based system and method for extracting natural rubber latex from the guayule shrub.

BACKGROUND

The plant Hevea brasiliensis, also known as the "Hevea tree" or the "rubber tree," is a well-known source of natural rubber. Natural rubber consumption in the United States is largely derived from the Hevea tree. Rubber sources such as the Hevea tree, and other plants such as Ficus elastic or the "India rubber tree," and Cryptostegia grandiflora or the "Madagascar rubber vine," all produce natural rubber in the form of a sap containing rubber latex, which flows freely and can be recovered by tapping of the plant.

Various non-Hevea plants are also known to contain natural rubber. However, their rubber is usually stored within the individual cells of the plant, such as in the stems, roots or leaves. The latex in these non-Hevea plants cannot be accessed by tapping, and instead can only be accessed by breaking down the cell walls through physical or other means. For this reason, processes for the removal of rubber from non-Hevea plants are generally more complicated than processes for harvesting rubber from sap-producing sources such as Hevea trees.

A particular non-Hevea plant is *Parthenium argentatum*, commonly known as the guayule shrub. Historically, an overwhelming majority of the Hevea-derived natural rubber imported by the United States originates in Indonesia, Malaysia and Thailand. However, natural rubber from the guayule shrub can be grown in southwestern United States and northern Mexico, and thus is desirable in the United States as a domestic alternative to Hevea-derived natural rubber.

Several methodologies and associated variations exist for the isolation of guayule rubber from guayule shrubs. The methodologies can be classified in three categories: flotation; latex process; and solvent process.

An example of a flotation process is found in U.S. Pat. No. 2,408,853 to Hoover et al, which describes how crushed or cut defoliated guayule shrubs are pebble milled in a slurry to form "rubber worms," which are then separated by flotation. Hoover et al. also describes the purification of the rubber worms by a fermentation method.

The latex process is described in U.S. Pat. No. 5,580,942 to Cornish. The Cornish patent describes a process for the preparation of guayule latex by homogenizing the plants in an aqueous medium, filtering the homogenate and separating the rubber-containing phase from the aqueous phase by centrifugation.

In U.S. Pat. No. 4,136,131 to Buchanan, a solvent process is described in the form of a protocol for the extraction of guayule rubber from guayule shrubs. The Buchanan process comprises a size reduction of the guayule shrubs and shaping of the generated particles, and then a sequential extraction of resin and rubber with selected solvents.

Recovery of the natural rubber from rubber latex, regardless of the process used to extract the latex, can then be done by coagulation followed by extraction. For example, U.S. Pat. No. 8,815,965 to Cole et al. describes how non-Hevea latex can be contacted with organic solvents to yield a rubber-rich organic phase and a rubber-poor aqueous phase. Further processing of the organic phase (e.g., extraction and drying) provides solid guayule rubber.

Conventionally-processed guayule latex is normally obtained from the guayule plant using the techniques outlined in U.S. Pat. No. 5,580,942 to Cornish. The latex may be concentrated to at least 50% solids, although lower levels can be used. The latex is mixed with a solution of an inorganic salt, typically a calcium salt, which will destabilize the surfactant and result in coagulation to form solid rubber. The polymer can then be stabilized to prevent oxidation and allowed to dry.

Guayule latex normally contains an equivalent amount of a resin, which must be removed in order to provide a natural rubber with desirable physical properties. Known processes for dealing with resin removal include U.S. Pat. No. 2,618,670 to Clark, the entire of disclosure of which is hereby incorporated herein by reference. The Clark patent describes how guayule resin can be extracted from guayule rubber bearing materials by using the methyl ethyl ketone/water azeotropic mixture as extraction medium. The U.S. Pat. No. 9,273,153 to Martin et al. also describes processing guayule latex in an extruder. In the Martin et al. patent, the guayule latex is fed in to an extruder in which coagulation, washing, and drying of the rubber are described. Although solvents and blends of solvents are mentioned by Martin et al., there are no examples, and no appreciation for the importance of choosing specifically a solvent system (blend) where the first solvent is configured to coagulate the latex, and the second is solvent configured to swell the resulting coagulum. In fact, solvent swelling of the coagulum is not disclosed by Martin et al.

There is a continuing need for a more efficient and effective system and method for obtaining rubber from non-Hevea sources such as the guayule shrub, which will result in superior natural rubber quality and usability. Desirably, the system and method facilitate coagulation and extraction of the natural rubber latex.

SUMMARY

In concordance with the instant disclosure, a more efficient and effective system and method for obtaining rubber from non-Hevea sources such as the guayule shrub, which will result in superior natural rubber quality and usability, and which facilitates coagulation and extraction of the natural rubber latex, has been surprisingly discovered.

In one embodiment, a latex processing method includes a step of mixing a latex and at least one solvent blend in an extruder. The at least one solvent blend is configured to remove resin found in the latex and to coagulate the latex to form a coagulum. The at least one solvent blend includes a first solvent and a second solvent. The first solvent is configured to coagulate the latex, and the second is solvent configured to swell the resulting coagulum. The solvent blends achieve different solubility parameters such that the rubber is not miscible in the solvent phase, and such that the swell is carefully controlled.

In another embodiment, a latex processing method involves mixing a latex and a series of solvent blends at different locations along a length of an extruder, in order to coagulate the latex to form a coagulum and to remove resin found in the latex. The series of solvent blends include a first solvent configured to coagulate the latex and a second solvent configured to swell the resulting coagulum. The solvent blends achieve different solubility parameters such that the coagulum is not miscible in the solvent phase and such that the swell is carefully controlled. The series of solvent blends including distinct blends of the first solvent and the second solvent, introduced at the different locations, and having different ratios of the first solvent and the second solvent.

In yet another embodiment, a latex processing system includes an extruder having a first mechanical filter, a second mechanical filter, and a third mechanical filter. The extruder has a first end and a second end, and at least one screw. Although a single screw may be used, a twin screw extruder may be preferred in certain embodiments. The extruder further has a plurality of process zones that are positioned between the first end and second end. The plurality of process zones includes a coagulation zone, a first wash zone, and a second wash zone. The coagulation zone is configured to receive a latex and a first solvent blend and to coagulate the latex into a coagulum. The first wash zone is in communication with the coagulation zone and configured to receive the coagulum and a second solvent blend. The second wash zone is in communication with the first wash zone and configured to receive the coagulum and a third solvent blend. The first mechanical filter is in communication with the coagulation zone, and is configured to remove at least a portion of the first solvent blend from the coagulum in the coagulation zone. The second mechanical filter is in communication with the first wash zone, and is configured to remove a least a portion of the second solvent blend from the coagulum in the first wash zone. The third mechanical filter is in communication with the second wash zone, and is configured to remove at least a portion of the third solvent blend from the coagulum in the second wash zone.

In a further embodiment, a latex processing methods includes a step of mixing the latex and the first solvent blend in the coagulation zone of the extruder to form the coagulum. A portion of the first solvent blend in the coagulation zone is then removed using the first mechanical filter. The coagulum is then washed with the second solvent blend at the first wash zone. A portion of the second solvent blend is then removed at the first wash zone using the second mechanical filter. The coagulum is then washed with the third solvent blend at the second wash zone. A portion of the third solvent blend is then removed at the second wash zone using the third mechanical filter. A vacuum is then applied to the extruder at a location downstream from the third mechanical filter, in order to extract any residual amounts of the first solvent blend, the second solvent blend, and the third solvent blend. The coagulum is then extruded through the second end of the extruder to provide a natural rubber.

In an exemplary embodiment, the disclosure includes a method for preparing guayule natural rubber from guayule latex, using a screw extruder and solvent blends in order to remove the resin. The method involves mixing the latex with a solvent blend (e.g., acetone/hexane) in a coagulation zone of the extruder. Guayule natural rubber is soluble in hexane but insoluble in acetone. The acetone is used to coagulate the latex into guayule natural rubber. The hexane is used to swell the resulting guayule natural rubber, in order to make it softer and increase its mechanical interaction with the extruder for more efficient resin extraction. The resin is removed together with the majority of the solvent through mechanical filters after the coagulation zone. Vacuum is used to reduce the total volatiles to less than 1% before the rubber leaves the extruder for end use.

Advantageously, the ratio of acetone/hexane is selected so that the coagulum is soft enough to be processed (i.e., the resin is extracted), but not so soft that it either dissolves in the solvent or is pushed through the filters. The hexane wet fraction is high enough so as to induce a desired amount of swell. It has been surprisingly found that the hexane weight fraction must be particularly from about 1% to about 53%, and more particularly between about 20% and about 40% for this purpose. The mass swell ratio (i.e., the weight of swollen rubber at equilibrium/weight of dry rubber), which increases in a non-linear relationship with increasing hexane content in the solvent blend, is also between 1.3 and 2.5, particularly between 1.4 and 2.0, and most particularly between 1.5 and 1.6. In a particular example, this mass swell ratio is obtained by a ratio of 79-84% acetone/21-16% hexane.

Additionally, the extruder temperature during processing is also controlled in order to minimize loss of the coagulum through the filters. One of ordinary skill in the art may select a suitable temperature or range of temperatures for the extruder during the extrusion process, as desired.

The ratio of acetone/hexane is also changed along the length of the extruder in order to optimize processing and removal of the resin. For example, at the coagulation zone the ratio may be 84/16 to facilitate coagulation, at the first wash zone the ratio may be 79/21 to facilitate swell, and at the second wash zone the ratio may be 100/0 in order to maintain swell and prevent over-softening or dissolving of the rubber, which would otherwise result in the loss of the rubber through the filters. In other words, the 100/0 ratio may reduce the swell to a minimum so as to expel the solvent, which contains the dissolved resin, from the swollen mass.

BRIEF DESCRIPTION OF THE DRAWINGS

The above, as well as other advantages of the present disclosure, will become readily apparent to those skilled in the art from the following detailed description, particularly when considered in the light of the drawings described herein.

DETAILED DESCRIPTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical unless otherwise disclosed.

The present disclosure includes a system and method for both resin removal and coagulation of guayule latex in an extruder. The disclosure involves an application of an unexpected and surprisingly discovered criticality of solvent blends for coagulant and wash solvents in the extruder, as well as the extruder screw speed, to effectively and efficiently remove the guayule resin during the coagulation process.

Figure 1:
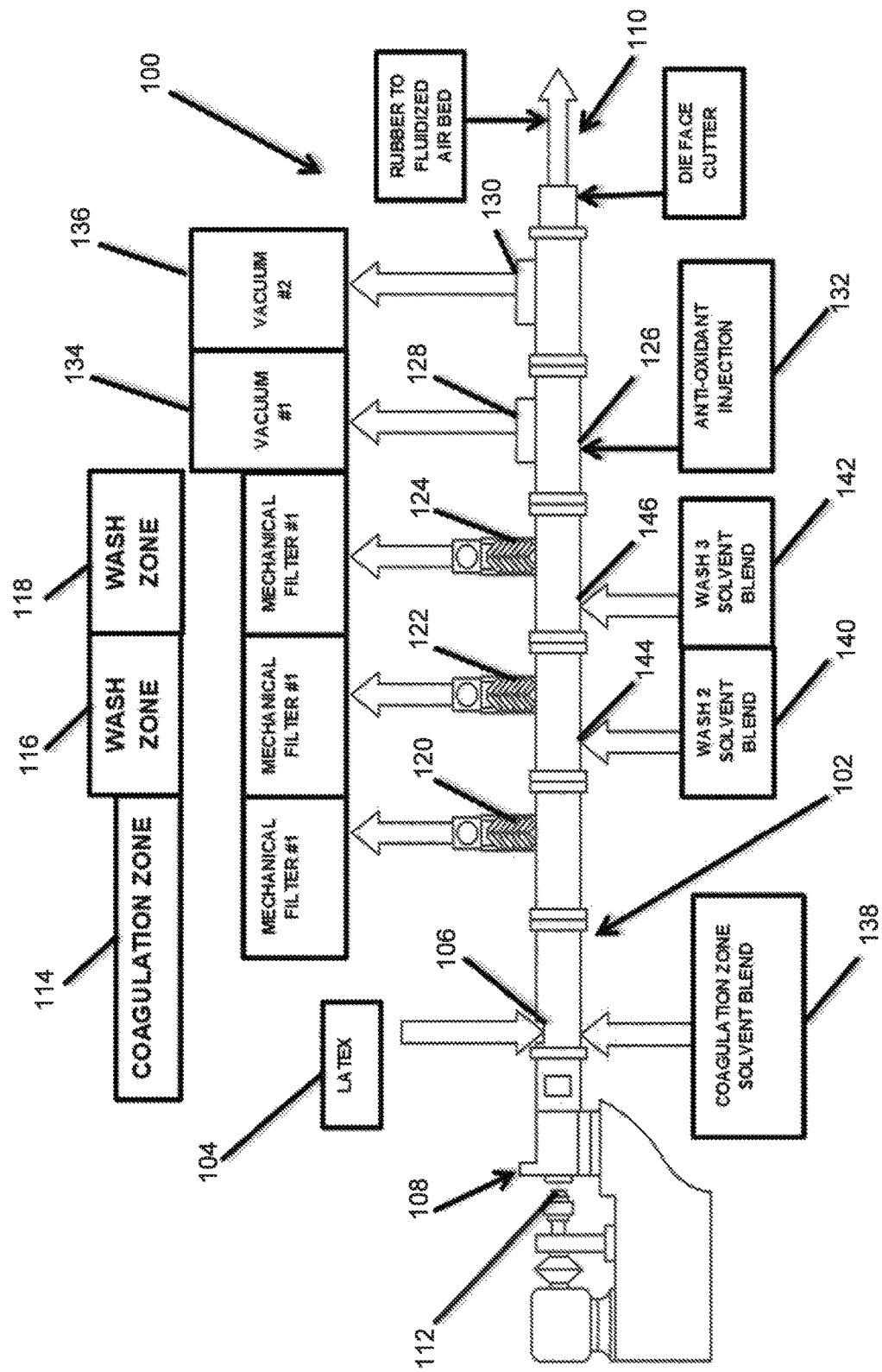
FIG. 1 is schematic diagram of an extruder system for removal of guayule resin and coagulation of guayule rubber latex into natural rubber, according to one embodiment of the disclosure.

FIG. 1 shows a schematic representation of a system 100 according to an embodiment of the present disclosure, including an extruder 102 for receiving guayule latex 104 at an inlet port 106 of the extruder 102. The extruder 102 has a first end 108 and a second end 110, and at least one screw 112. An exemplary description of extrusion, coagulation, and de-volatilization operations, including typical extruder configurations, is described in "Direct Extrusion of Polymer Latex Emulsions" by Russell Nichols, Richard Senn and Farokh Kheradi in Advances in Polymer Technology, vol. 3, n 1, p 41-49, 1983, the entire disclosure of which is hereby incorporated herein by reference. A process for converting an emulsion of a polymer into a solid polymer, dewatering the polymer, and drying the polymer is also described in U.S. Pat. No. 3,742,093 to Skidmore, the entire disclosure of which is hereby incorporated herein by reference.

In particular, the extruder 102 further has a plurality of process zones disposed between the first end 108 and the second end 110. The plurality of process zones of the extruder 102 includes a coagulation zone 114 where the guayule latex 104 is processed to form a coagulum, a first wash zone 116, and a second wash zone 118. Each of the coagulation zone 114, the first wash zone 116, and the second wash zone 118 also has an associated filter 120, 122, 124. Although a variety of filter types may be used, mechanical filters may be particularly useful for the present application. Exemplary mechanical filters 120, 122, 124 are described in U.S. Pat. No. 4,110,843 to Skidmore, and in "Direct Extrusion of Polymer Latex Emulsions" by Russell Nichols, Richard Senn and Farokh Kheradi in Advances in Polymer Technology, vol. 3, n 1, p 41-49, 1983, the entire disclosures of which are hereby incorporated herein by reference. For example, the mechanical filters 120, 122, 124 may be small twin screw extruders which serve outlets for excess solvent, but which forces entrained solids back into the main barrel of the extruder 102. One of ordinary skill in the art may also use other suitable types of filters within the scope of the present disclosure, as desired.

The extruder 102 is also provided with at least one port 126, 128, 130 after the process zones through which additional ingredients such as antioxidants 132 may be injected into the extruder 102, or on which a vacuum 134, 136 may be pulled in order to further extract solvents and dry the coagulum formed from the guayule latex 104.

The guayule latex 104 can be introduced through the inlet port 106 into the coagulation zone 114 together with a first solvent blend 138. The first solvent blend 138 is configured to coagulate the guayule latex 104 to form the coagulum, to remove resin that is naturally present in the guayule latex 104, and to induce swell in the resulting coagulum in order to facilitate a processing of the coagulum in the extruder 102. A second solvent blend 140 and a third solvent blend 142 are introduced through ports 144, 146 at the first wash zone 116 and the second wash zone 118, respectively.

The first solvent blend 138, the second solvent blend 140 and the third solvent blend 142 are further configured to remove residual resin from coagulum produced by the coagulation of the latex 104, while also maintaining the swell of the coagulum at a level that facilitates the processing, while further militating against an over-softening and inadvertent removal of the coagulum from the extruder 102 through the mechanical filters 120, 122, 126.

In a particular example, the first, second, and third solvent blends 138, 140, 142 include acetone and hexane, at various predetermined ratios. However, other types of solvents and blends are contemplated and considered to be within the scope of the present disclosure. More than three distinct solvent blends are also contemplated. One of ordinary skill in the art may selected suitable solvent compositions for the first, second, and third solvent blends 138, 140, 142, and other blends, as desired.

It has been surprisingly found that the use of just acetone as the solvent does not effectively remove the resin from the guayule latex 104. This criticality of the solvent blend compositions is shown below in TABLE 1, which is described with reference to FIG. 1.

TABLE 1

Criticality of the solvent blend compositions

|  | Example #1 | Example #2 |
|---|---|---|
| Coagulant | 100% Acetone | 71% Acetone-29% Hexanes |
| First Wash | 100% Acetone | 85% Acetone-15% Hexanes |
| Second Wash | 100% Acetone | 95% Acetone-5% Hexanes |
| Residual guayule resin | 11.1% | 3.7% |
| Mooney viscosity ML1 + 4 | 65 | 78 |
| Extraction efficiency | 26% | 75% |

Without being bound to any particular theory, guayule natural rubber is soluble in hexanes while it is insoluble in acetone. There exists acetone/hexanes blends in which guayule natural rubber is soluble, and blends in which guayule natural rubber is insoluble. When the hexanes weight fraction in the solvent is lower than about 53%, it has been found that guayule natural rubber is not soluble in the acetone/hexanes solvent blend. Instead, the rubber swells to a certain extent, reflecting the polymer-solvent interaction. The mass swell ratio (i.e., weight of swollen rubber at equilibrium/weight of dry rubber) increases with increasing hexanes content, and the relationship is non-linear.

As used herein, the term "extraction efficiency" means a ratio of resin removed by extraction to total resin content. For the example in TABLE 1, the initial resin content was about 15% by weight on a dry basis. Thus, the extraction efficiency of Example #2 was significantly greater than the extraction efficiency associated with Examiner #1, which used pure acetone. This was a surprising and unexpected result, in that pure acetone was previously believed, prior to the present invention, to be sufficient by itself in extraction of the resin.

As the mass swell ratio increases, the hardness and viscosity of the material decreases, and thereby affecting the mechanical interaction of the material in the extruder. Various mass swell ratios involving solvent blends of acetone and hexane are shown below in TABLE 2.

TABLE 2

Mass swell ratios

| Acetone | Hexanes | Guayule rubber mass swell ratio |
|---|---|---|
| 100% | 0% | 1.19 |
| 95% | 5% | 1.31 |
| 90% | 10% | 1.41 |
| 85% | 15% | 1.55 |
| 80% | 20% | 1.67 |
| 75% | 25% | 1.85 |
| 70% | 30% | 2.10 |

TABLE 2-continued

Mass swell ratios

| Acetone | Hexanes | Guayule rubber mass swell ratio |
|---|---|---|
| 65% | 35% | 2.51 |
| 60% | 40% | 3.05 |
| 55% | 45% | 4.46 |
| 50% | 50% | 5.69 |
| 48% | 52% | 9.92 |
| 47% | 53% | 14.59 |

In order to achieve efficient resin extraction from the coagulum, the latter must be soft enough so the mechanical action of the screw(s) of the extruder 102 induce a large extent of surface renewal for efficient mass transfer. Although, if the coagulum is too soft, the mechanical filters 120, 122, 124 are unable to retain it in the extruder barrel (i.e., losses). It has been determined that a mass swell ratio between 1.5 and 1.6 at the coagulation and first wash zones is desirable.

In particular embodiments, maintaining a hexane weight fraction in acetone of about 16% throughout the extruder 102 processing zones may be preferred. For example, the first solvent blend 138 may have a hexane weight fraction in acetone from about 0% to about 40%, the second solvent blend 140 may have a hexane weight fraction in acetone from about 5% to about 25%, and the third solvent blend 142 may have a hexane weight fraction in acetone from about 10% to about 20%. One of ordinary skill in the art may select other suitable weight fractions of hexane in acetone, as desired.

The data shown below in TABLE 3 also exemplifies the criticality of extruder screw speed to the system and method of the present disclosure. It should be appreciated that the details provided in TABLE 3 are non-limiting, however, and are provided merely as an example of an optimum operating range for a particular extruder type. One of ordinary skill in the art understand that actual optimum operating ranges will be a function of a specific extruder 102 selected for the coagulation and resin removal processes.

TABLE 3

Criticality of extruder screw speed

| | Example #1 | Example #2 | Example #3 | Example #4 |
|---|---|---|---|---|
| Coagulant | | 84% Acetone-16% Hexanes | | |
| First Wash | | 79% Acetone-21% Hexanes | | |
| Second Wash | | 100% Acetone-0% Hexanes | | |
| Screw Speed | 35 rpm | 50 rpm | 75 rpm | 100 rpm |
| Residual guayule resin | 5.6% | 4.1% | 2.1% | 1.3% |
| Mooney viscosity ML1 + 4 | 83 | 86 | 95 | 98 |
| Extraction efficiency | 63% | 73% | 86% | 91% |

With respect to TABLE 3, it should also be understood many parameters influence extraction efficiency. However, it has been surprisingly found that solvent blend compositions are a primary factor. Other parameters comprise screw design, screw speed, flow rates, and barrel temperature. Additionally, it is believed that optimum values for this process are valid for a latex at 45% moisture.

Figure 2:
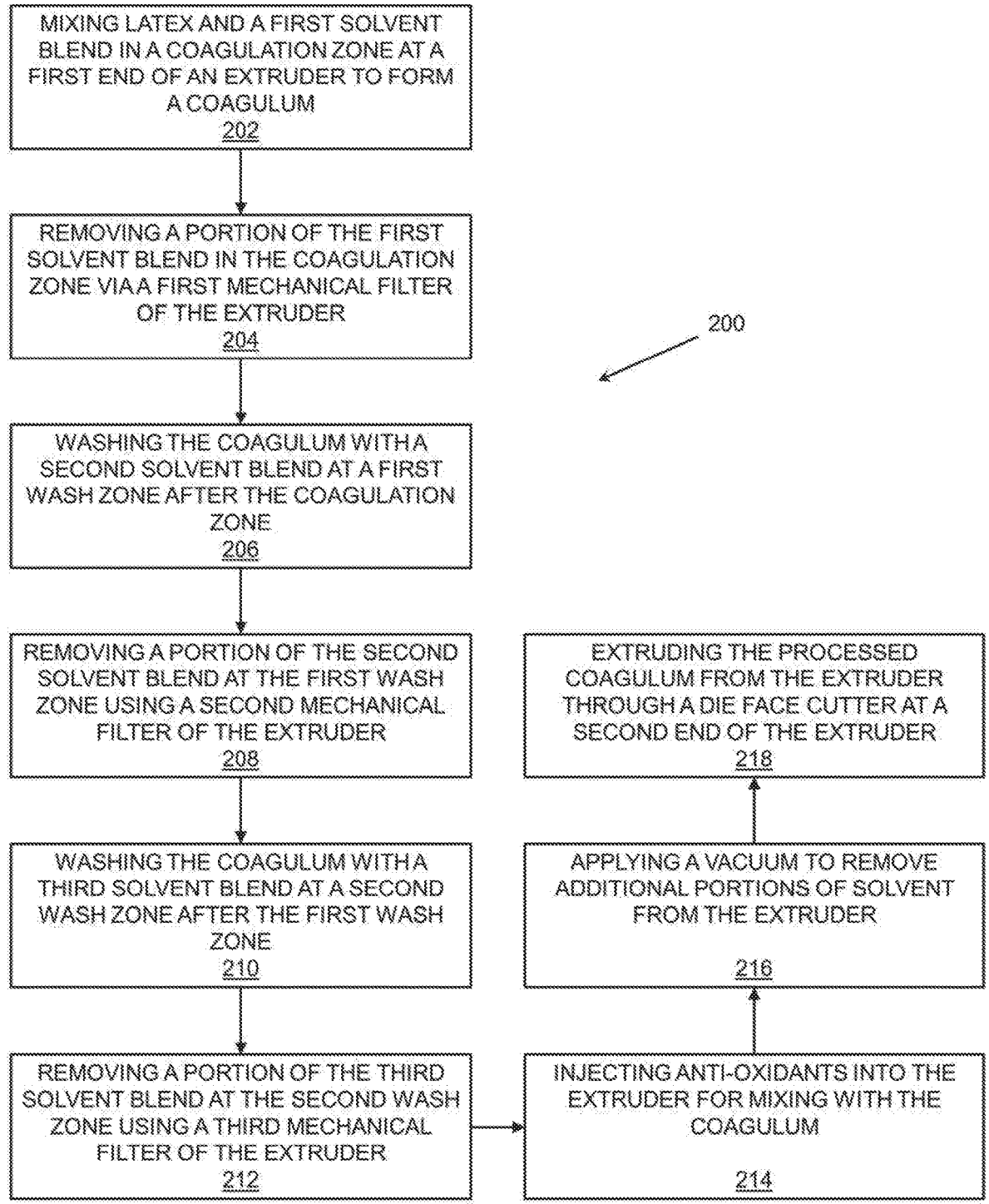
FIG. 2 is a flow diagram depicting a method for removal of guayule resin and coagulation of guayule rubber latex into natural rubber, according to one embodiment of the disclosure.

In operation, as shown in FIG. 2, the latex processing method 200 of the present disclosure includes a first step 202 in which the guayule latex 104 is mixed with the first solvent blend 138 at the first end 108 of the extruder 102. The first solvent blend 138 is configured to coagulate the guayule latex 104 to form the coagulum. Advantageously, the first solvent blend 138 is also configured to extract at least a portion of the resin that is naturally present in the guayule latex 104. In a particular embodiment, the first solvent blend 138 is a mixture of about 71% acetone and about 29% hexane.

The resulting mixture of coagulum and the first solvent blend 138 is then advanced along the length of the extruder 102 through the coagulation zone 114 to a first mechanical filter 120. At least a portion of the first solvent blend 138, now containing the resin extracted from the guayule latex 104, is then removed from the extruder 102 through the first mechanical filter 120 in a step 204.

The coagulum and residual amounts of the first solvent blend 138 are then advanced through the extruder 102 to the first wash zone 116. The coagulum is mixed and thereby "washed" with the second solvent blend 140 at the first wash zone 116, in a step 206. It should be appreciated that the mechanical action of the screw within the extruder, interacting with the swelled coagulum, functions to further agitate or breakup the coagulum during the washing. The speed of the extruder screw is also controlled in order to optimize the mechanical agitation during this stage. This mechanical agitation of the coagulum facilitates even further removal of any residual resin in the coagulum, and allows the residual resin to be extracted by the second solvent blend 140.

The resulting mixture of coagulum and the second solvent blend 140 is then advanced along the length of the extruder 102 through the first wash zone 116 to the second mechanical filter 122. At least a portion of the second solvent blend 140, now containing the resin extracted from the coagulum, is then removed from the extruder 102 through the second mechanical filter 122 in a step 208.

The coagulum and residual amounts of the second solvent blend 140 are then advanced through the extruder 102 to the second wash zone 118. The coagulum is mixed and thereby "washed" with the third solvent blend 142 at the second wash zone 118, in a step 210. As with the washing of step 206, it should be appreciated that the mechanical action of the screw within the extruder 102, interacting with the swelled coagulum, functions to further agitate the coagulum during the washing of step 210. The speed of the extruder screw is also controlled in order to optimize the mechanical agitation during this stage. This mechanical agitation of the coagulum facilitates even further removal of any residual resin in the coagulum, and allows the residual resin to be extracted by the third solvent blend 142.

The resulting mixture of coagulum and the third solvent blend 142 is then advanced along the length of the extruder 102 through the second wash zone 116 to the third mechanical filter 124. At least a portion of the third solvent blend 142, now containing the resin extracted from the coagulum, is then removed from the extruder 102 through the third mechanical filter 124 in a step 212.

At this stage, it should be appreciated that the coagulum is substantially free of the resin that is otherwise naturally found in the guayule latex 104, for example, as shown in TABLE 4 below.

TABLE 4

Average residual resin content for guayule natural
rubber processed according to the present disclosure
relative to conventionally-processed guayule natural rubber
Guayule Rubber Raw Materials

|  | Supplier #1 | Supplier #2 | |
| --- | --- | --- | --- |
| Rubber Form | Solid | Latex | Solid |
| Process | Conventional | Proprietary | Conventional |
| Latex Composition |  |  |  |
| Water | — | 45% | — |
| Solids | — | 55% | — |
| Resin | — | 15% of solids | — |
| Solid Rubber Properties |  |  |  |
| Average Mooney Viscosity | 70 | 100 | 77 |
| Average Residual Resin | 2 wt % | 1 wt % | 3 wt % |
| Gel Content | ~0% | <10% | <10% |

Further ingredients to modify or adjust the properties of the resulting coagulum, such as anti-oxidants as a non-limiting example, are the optionally injected into the extruder at a step 214.

At a step 216, the vacuum 134, 136 may be applied to the extruder 102 in order to extract remaining solvents and further dry the coagulum before extrusion through a die face cutter in a step 218. The coagulum or natural rubber may then be delivered to a fluidized air bed, for example, for additional processing or packaging for later end use.

Advantageously, the system 100 and method 200 of the present disclosure are more efficient and effective for extracting rubber from non-Hevea sources such as the guayule shrub. This results in superior natural rubber quality and usability.

While certain representative embodiments and details have been shown for purposes of illustrating the invention, it will be apparent to those skilled in the art that various changes may be made without departing from the scope of the disclosure, which is further described in the following appended claims.

What is claimed is:

1. A latex processing method, comprising a step of mixing a latex containing a natural rubber and at least one solvent blend in an extruder having a plurality of zones to remove resin found in the latex and to coagulate the latex to form a coagulum, wherein the at least one solvent blend includes a first solvent configured to coagulate the latex and a second solvent configured to swell the resulting coagulum,
wherein the at least one solvent blend does not dissolve the natural rubber but swells the natural rubber,
wherein the at least one solvent blend includes a series of solvent blends, the series of solvent blends including distinct blends of the first solvent and the second solvent, each of the distinct blends introduced at one of the plurality of zones in the extruder and having different ratios of the first solvent and the second solvent, a ratio of the first solvent to the second solvent increases through the series of solvent blends, the series of solvent blends including a first solvent blend of acetone and hexane with a hexane weight fraction in the acetone from greater than 0% to 53% and a second solvent blend of acetone and hexane with a hexane weight fraction in the acetone from 5% to 25%.

2. The latex processing method of claim 1, wherein the latex is a guayule latex.

3. The latex processing method of claim 1, wherein the series of solvent blends includes a third solvent blend having acetone and hexane with a hexane weight fraction in the acetone from 10% to 20%.

4. The latex processing method of claim 1, wherein the plurality of zones includes a coagulation zone and a first wash zone and each of the distinct solvent blends is configured to swell the coagulum to a mass swell ratio between 1.5 and 1.6 at the coagulation zone and the first wash zone.

5. The latex processing method of claim 1, wherein the extruder includes a filter, each of the first solvent blend and the second solvent blend is configured to swell the coagulum to a mass swell ratio between 1.5 and 1.6, and the filter is configured to retain the coagulum within a barrel of the extruder.

6. The latex processing method of claim 1, wherein the first solvent blend includes a hexane weight fraction in acetone from 0% to 40% and the second solvent blend includes a hexane weight fraction in acetone from 5% to 25%.

7. The latex processing method of claim 6, wherein the series of solvent blends includes a third solvent blend having acetone and hexane with a hexane weight fraction in the acetone from 10% to 20%.

8. The latex processing method of claim 1, wherein the extruder is operated at an rpm value configured to provide a Mooney viscosity of 98.

9. The latex processing method of claim 1, wherein the latex containing the natural rubber includes 45% moisture.

10. The latex processing method of claim 1, further comprising apply a vacuum to the extruder to extract remaining solvent from the coagulum.

11. The latex processing method of claim 1, further comprising extruding the coagulum through a die face cutter.

12. A latex processing method, comprising:
providing an extruder including a first end and a second end, and at least one screw, the extruder comprising a plurality of process zones positioned between the first end and second end, the plurality of process zones including a coagulation zone, a first wash zone, and a second wash zone, the coagulation zone configured to receive a latex and a first solvent blend and to coagulate the latex into a coagulum, the first wash zone in communication with the coagulation zone and configured to receive the coagulum and a second solvent blend, and the second wash zone in communication with the first wash zone and configured to receive the coagulum and a third solvent blend, a first mechanical filter in communication with the coagulation zone, each of the first solvent blend, the second solvent blend, and the third solvent blend includes a first solvent configured to coagulate the latex and a second solvent configured to swell the resulting coagulum, the first solvent blend, the second solvent blend, and the third solvent blend form a series of solvent blends and a ratio of the first solvent to the second solvent increases through the series of solvent blends, wherein the first solvent blend is acetone and hexane with a hexane weight fraction in the acetone from greater than 0% to 40%, the second solvent blend is acetone and hexane with a hexane weight fraction in the acetone from 5% to 25%, and the third solvent blend is acetone and hexane with a hexane weight fraction in the acetone from 10% to 20%;
mixing the latex and the first solvent blend in the coagulation zone of the extruder to form the coagulum;

removing a portion of the first solvent blend in the coagulation zone using the first mechanical filter;

washing the coagulum with the second solvent blend at the first wash zone;

removing a portion of the second solvent blend at the first wash zone using the second mechanical filter;

washing the coagulum with the third solvent blend at the second wash zone;

removing a portion of the third solvent blend as the second wash zone using the third mechanical filter;

applying a vacuum to the extruder at a location upstream from the third mechanical filter to extract extra residual amounts of the first solvent blend, the second solvent blend, and the third solvent blend; and extruding the coagulum through the second end of the extruder to provide a natural rubber.

13. The latex processing method of claim 12, wherein the latex is a guayule latex.

14. The latex processing method of claim 12, wherein each of the first solvent blend and the second solvent blend is configured to swell the coagulum to a mass swell ratio between 1.5 and 1.6.

* * * * *